United States Patent [19]

Ruhenstroth-Bauer et al.

[11] 4,094,759
[45] June 13, 1978

[54] METHOD FOR SIMULTANEOUS QUANTITATIVE ANALYSIS OF SEVERAL CONSTITUENTS IN A SAMPLE

[75] Inventors: Gerhard Ruhenstroth-Bauer, Grafelfing; Reiner Scherer, Munich, both of Germany

[73] Assignee: Max-Planck-Gesellschaft zur Forderung der Wissenschaften e.v., Gottingen, Germany

[21] Appl. No.: 758,735

[22] Filed: Jan. 12, 1977

Related U.S. Application Data

[62] Division of Ser. No. 646,391, Jan. 2, 1976, Pat. No. 4,018,662.

[30] Foreign Application Priority Data

Jan. 3, 1975 Germany .............................. 2500218

[51] Int. Cl.$^2$ ............................................. G01N 27/26
[52] U.S. Cl. ........................... 204/180 G; 204/180 S; 204/299 R
[58] Field of Search ................ 204/180 S, 180 G, 299

[56] References Cited

U.S. PATENT DOCUMENTS

| 3,255,100 | 6/1966 | Raymond | 204/180 G |
| 3,567,611 | 3/1971 | Michel et al. | 204/180 G |
| 3,736,100 | 5/1973 | Rains | 204/299 X |
| 3,865,712 | 2/1975 | Davies | 204/299 |
| 3,988,230 | 10/1976 | Krotz | 204/180 G |

*Primary Examiner*—Arthur C. Prescott
*Attorney, Agent, or Firm*—Edwin E. Greigg

[57] ABSTRACT

A method for simultaneous qualitative and quantitative analysis of antigens or antigen-effective substances in a sample provides placing the sample in a carrier medium through which it migrates toward a plurality of physically separate carrier strips. The medium on each strip contains a quantity of a specific ingredient, for example an antibody, which is expected to undergo a specific immunoreaction with one of the constituents in the sample, thereby producing a visible precipitate. The dimensions of the final precipitate then permit a direct measurement of the identified substance. A known concentration of a calibrating substance may be added to the sample to provide for calibration precipitates in the various strips. The apparatus for practicing the method includes a base plate on which the neutral, antibody-free carrier medium as well as the various strips containing media with antibodies or other immunoreactive ingredients are located. An electric field may be applied to aid in the migration of the sample in the medium.

10 Claims, 12 Drawing Figures

METHOD FOR SIMULTANEOUS QUANTITATIVE ANALYSIS OF SEVERAL CONSTITUENTS IN A SAMPLE

BACKGROUND OF THE INVENTION

This is a Division, of application Ser. No. 646,391 filed Jan. 2, 1976 now Pat. No. 4,018,662

The invention relates to a method and an apparatus for carrying out that method for the simultaneous specific and quantitative determination of several substances capable of immunoreaction. The substances are especially of the kind capable of effective antigen action and the sample migrates from an antibody-free carrier into a carrier containing further constituents which together with the substances to be determined, generate an immunoreaction. The substances which are to be analyzed form precipitates and the extent of migration of the sample takes place in the direction of an electric field which extends over the sample and over the carrier. An apparatus for carrying out this method, as well as advantageous uses of the method, are also part of the invention.

An important field of application of a method such as described above is, for example, the quantitative determination of proteins in blood plasma. Such plasma proteins are for example: Prealbumin, Albumin, α-Lipoprotein, α-I-Antitrypsin, α-I-B-Glykoprotein, Gc-Globulin, Coeruloplasmin, α-2-Macroglobulin, Pseudocholinesterase, hemopexin, Transferrin, β-Lipoprotein, Haptoglobin, Orosomucoid, Antitrypsin, C-reactive protein, Fibrinogen, Plasminogen, IgG, IgM, IgA, IgD. The quantitative determination of these proteins in many cases permits differential diagnostic conclusions to be made or else, when the diagnosis has been made, it yields further information regarding the progress and prognosis of a disease (H. H. Märki, Analytische Methoden zur Darstellung der Serumeiweisskorper und ihre Aussagemöglichkeiten für Klinik und Praxis, Deutsches Medizinisches Journal, 1972 (Jg. 23), S. 317 ff.; H. J. Braun, Immunglobuline, Paraproteine und Blutfarbstoff bindende Proteine und ihre Bedeutung fur die Klinik, Deutsches Medizinisches Journal, 1972 (Jg. 23) S. 227 ff.; C.-O. Kindmark + C.-B. Laurell, "Sequential Changes of the Plasma Protein Pattern in Inoculation Hepatitis, Scand. J. clin. Lab. Invest. 29, suppl. 24, 105–115 (1972); J. S., Hepatitis: IgA-Mangel erhoht Risiko, SELECTA 41, S. 3574 (1974); as well as the research of R. Scherer, A. Moratescu, and G. Ruhenstroth-Bauer, "Die spezifische Wirkung der Plasma-Proteine bei der Blutkörperchensenkung").

Several methods have been published for the quantitative determination of single substances (antigens) which produce immunoreaction with antibodies or, again, methods for the quantitative determination of substances (antibodies) which produce immunoreaction with antigens. Such methods are disclosed for example in W. Becker, B. Rapp, H. G. Schwick und K. Störiko, "Methoden zur quantitative Bestimmung von Plasmaproteinen durch Immunpräzipitation", Zeitschrift für klinische Chemie und klinische Biochemie, 1968, Heft 3, S. 113–122; W. Becker, "Methoden der qualitativen und quantitativen Immun-Elektrophorese", Hrsg. Behringwerke AG, Frankfurt, 1972; Prospekt "DAKO-Immunoglobulins" der DAKOPATTS A/S., Dänemark, 1972. All these methods are based on the principle of immunodiffusion and/or electrophoresis.

When the concentration of antigens is to be determined by the method of immunodiffusion, the antigens contained within a sample diffuse into a carrier, for example a layer of agarose gel. The carrier contains only a particular antibody specific to a particular antigen. When antigens and antibodies make contact within the carrier, they react and form a complex which is precipitated within the carrier. The diffusion process proceeds until the specific antigen within the sample has been entirely used up by precipitation with the specific antibody in the carrier. Any remaining antigens within the sample can continue to diffuse into the carrier without hindrance and they form no precipitate. The area within the carrier in whch a precipitate is formed can be made visible by staining; for example in the so-called radial immunodiffusion process, this area is circular, i.e., it forms a circular zone around the application point at which the sample was applied to the carrier. The dimension of this area in which a precipitate was formed is thus a measure for the concentration of that antigen within the sample against which the antibody contained within the carrier was specifically directed.

In principle, this method may be used for a quantitative determination of all such antigens against which specific antibodies are known or against which specific antibodies can be produced. However, this method is very time-consuming and does not permit the simultaneous determination of several antigens.

The above-described method may be accelerated by the use of electrophoresis. Use is made of the fact that, under certain ambient conditions, antigens carry an electric charge. If an electric field is applied in the vicinity of the carrier, the electrically charged antigens pass through a substantially larger path within the carrier than would be the case in pure diffusion.

In the general practice, several methods for the determination of the concentration of individual antigens are used;

(a) In the so-called acetate foil electrophoresis a sample (generally human serum) is split up, by an electric field adjacent to the foil, according to the different migration velocities of the individually contained components (antigens). After the separation, the sample is stained and is evaluated photometrically. The separation process normally used in clinical practice only determines a few groups, each of which has the same electrophoretic migration characteristics. Thus the differentiation is confined to a determination of $\alpha$, $\beta$, $\gamma$-Globulin and Albumin. Any quantification within these groups, i.e., the determination of the individual antigens (proteins) contained within each group is not possible by this method.

(b) In the process of radial immunodiffusion, the antigens within a sample diffuse from a cylindrical starting orifice in the radial direction into a layer of agarose gel of uniform thickness which contains antibodies. Thus, a cylindrical precipitate is formed around the starting orifice. When the concentration of antibodies in the layer of agarose gel is known, the circular area of the precipitate at the termination of the diffusion process is a measure of the quantity of antigen contained in the sample.

This method normally employs immunodiffusion plates having several starting orifices. In order to obtain a reference curve, several of these starting orifices are filled with different concentrations of a standard solution of known concentration and containing a particular antigen, namely that antigen against which the carrier contains antibodies. The remaining starting orifices are filled with different samples whose content of the same antigen is to be determined. When the diffusion process is complete, (after approximately 48 to 72 hours) the areas of the precipitates are measured and the measured values of the different concentrations of the standard solution represent a reference curve. This reference curve is used to determine the concentration of the particular antigens in the sample against which the antibody in the carrier is directed.

A disadvantage of this method is, first of all, the relatively long duration of the complete formation of the precipitate, i.e., 48 to 72 hours. Furthermore, this method is capable of measuring only the concentration of a single specific antigen at one time. If the concentration of several specific antigens is to be determined, the above-described process must be repeated for each antigen. This method is thus very time and labor consuming.

(c) In the so-called rocket immuno-electrophoresis, the disadvantage of great time consumption can be avoided in that the immuno-precipitation is accelerated by the application of an electric field. Just as in the radial immunodiffusion process, individual orifices in a plate, which has a surface carrier of agarose gel, are filled with different concentrations of a standard preparation so as to obtain a reference curve, and several samples with unknown content of a particular antigen are then introduced. After the application of an electric field, the sample migrates from the starting orifices into the carrier which contains antibodies that are specific against the antigen whose concentration is to be measured. For example, if the sample is serum, the antibodies would be specific against a serum protein. The migration of the proteins in the electric field results in precipitates which resemble "rockets" whose height is a measure of the concentration of those antigens within the sample which have undergone an immunoreaction with the antibodies contained in the carrier.

It is a disadvantage of this process that, just as in radial immunodiffusion, there is no possibility for the simultaneous determination of several antigens within a probe because the antibodies in the carrier which form the immunoreaction with the antigens are necessarily specific for only a particular antigen in the sample. In order to determine the concentration of, for example, ten different antigens within a sample (for example, ten different plasma proteins in a blood plasma of a patient) ten different carriers with different antibodies of the above-described type must be provided with samples and must be kept in electrophoretic chambers under electric current and subsequently individually evaluated. Until the present time, the great amount of instrumentation and apparatus, as well as the cost of labor, has prevented a wide use of this method in clinical practice.

(d) In the process of line immuno-electrophoresis (J. Kroll, Line Immunoelectrophoresis, in: M. H. Axelsen et al.: A Manual of Quantitative Immunoelectrophoresis, Oslo 1973, S. 61–67) a strip of gel which contains the sample with different antigens is contacted to several gel strips, each of which contains polyvalent antisera. After electrophoresis, the immunoreaction of the different antigens in the sample with the several antibodies contained in the polyvalent antisera form precipitate lines in each of the gel strips containing antisera. Since the gel strips containing the several polyvalent antisera are adjacent to one another, the precipitate lines in one strip extend into those of the neighboring strip and thus permit the comparison of the line spectra of the different polyvalent antisera.

(e) A known method of the above-described type, on which the present invention is based, is the so-called two-dimensional immuno-electrophoresis according to Clarke and Freeman. This method permits the simultaneous specific (qualitative) and quantitative determination of several antigens, i.e., for example several plasma proteins in blood plasma. In this method, the individual antigens (plasma proteins) are placed in a starting orifice in an agarose gel containing no antibodies and are separated purely electrophoretically in a particular direction (first dimension). Subsequently, he elecric field is applied in a second direction (second dimension) which is perpendicular to the first direction. Thus, the once separated antigens now travel in the direction of the second dimension into a carrier which contains antibodies against the various antigens. Thus, in the second dimension, there takes place the same process of electro-immunoprecipitation with the formation of bell-shaped precipitates which overlap. As before, the area of precipitation is a measure of the concentration of the particular antigen (plasma protein) in the applied sample. It is not sufficient however, as in rocket electrophoresis, merely to measure the height; rather the area must be measured and this may be done either by planimetry or after transfer of the outline to paper of normalized thickness by cutting out the figure and weighing it.

The disadvantage of this known method is the extremely great time consumption associated with an evaluation of the precipitates. A further disadvantage is that it is extremely difficult to make a correct interpretation of the resulting, very complicated appearance of the electrophoretic picture, i.e., to associate the different areas of precipitate with the correct antigens (plasma proteins). This is extremely difficult and requires a great deal of experience, particularly, when the elecrophoretic picture is substantially different from the expected normal case, as will be true in serum samples taken from hospital patients, due to possible pathology.

In summary, the state of the art is such that the determination of several substances capable of an immunoreaction is extremely complicated, expensive and time consuming. The methods a,b,c, described above do not permit the simultaneous determination of several substances within a sample. The method d does permit simultaneous determination but, as has already been mentioned, has the disadvantage that the formation of the precipitate areas to be evaluated takes a very long time and that the evaluation of the precipitates involves a number of very difficult questions of interpretation and identification, particularly in pathologically altered patient sera, while the required determination of the precipitate areas, either by measurement or by weighing, is extremely circuitous and time-consuming. It is these disadvantages which are the primary reason that the differential diagnostic methods based on the quantitative determination of several defined antigens, which are available in preliminary form, have been used until the present time only in highly specialized laboratories and require specially trained operators.

OBJECT AND SUMMARY OF THE INVENTION

It is a principal object of the invention to provide a method for the simultaneous determination of the type and quantity of substances in a biological sample. The method permits a substantially simpler and faster evaluation than has heretofore been possible in the methods described under subparagraph d above.

It is a further principal object of the invention to provide an apparatus for carrying out the method described by the invention.

These and other objects are attained by the invention by providing that the sample is applied to a carrier free from antibodies and migrates therefrom into several different carriers each of which contains different substances which form reactions and precipitates which are specific, in each case, to the constituents of the sample. The apparatus for carrying out this method provides a carrier of material free from antibodies which includes a well or opening for receiving the sample and several other carriers each of which contains different substances for forming precipitates with each of the constituents of the sample.

The substances whose presence in the sample is to be determined by the method and the apparatus according to this invention are all those substances which form an immunoreaction, i.e., which form precipitates with other substances, for example antigens forming an immunoreaction with antibodies or antibodies with antigens. The physical extent of the precipitates thus formed can be determined, if necessary after staining. Thus, the substances in which the application finds use could also be described encompassingly as "antigen effective" or "antibody effective". In the first case, the individual types of antibodies which are directed against a particular one of several antigens contained in the sample. In the latter case, each of the carriers includes an antigen specific to one of the antibodies contained in the probe. A further important field of application in the first named case, as already mentioned, is the determination of a concentration of individual plasma proteins in blood plasma for purposes of differential diagnosis. In the last mentioned case, a field of application is the diagnosis of autoimmunizing diseases.

The method and apparatus of the invention eliminates the above-described disadvantages of the methods and apparatus known to the present state of the art in a surprisingly simple manner. It is required only that the sample to be analyzed is supplied into the appropriate well and, after a duration of approximately eight hours, the concentration of several substances can be determined and the number of substances can be quite large, up to twenty or more.

During the examination of blood plasma of patients, any deviations of the concentration of constituents from a particular nominal value can be recognized in as large a number as desired of diagnostically significant plasma proteins, merely by the inspection of a plate and without great expense.

Thus, the invention creates the necessary condition in the laboratory for carrying out appropriate serial tests such as are necessary for recognizing certain pathological, typical deviations of the concentration of several plasma proteins which could otherwise not even be recognized and, if the pathology has been recognized or can be developed, the possibilities for diagnosis could be used in the medicinal practice of physicians not part of a clinical environment.

The invention will be better understood as well as further objects and advantages thereof become more apparent from the ensuing detailed specification of two exemplary embodiments of the invention.

DESCRIPTION OF THE PREFERRED EMBODIMENTS

Turning now to FIGS. 1–4, there is shown a glass plate 1 on which there is provided a layer 2 of a width of approximately 1.5 centimeters consisting of agarose gel, free from antibodies. For the purpose of applying this layer 2, the agarose gel is poured onto the glass plate 1 in the form of the strip 2. Subsequently, the strip 2 is permitted to dry. The strip 2 forms an antibody-free carrier on the glass plate 1. The strip 2 is provided with a recess in the form of a groove or a well 3. This may be done by pressing, scraping or the like. The well 3 serves to receive a solution of sample, thus, for example, a blood plasma sample, etc.

Figures 1, 4:
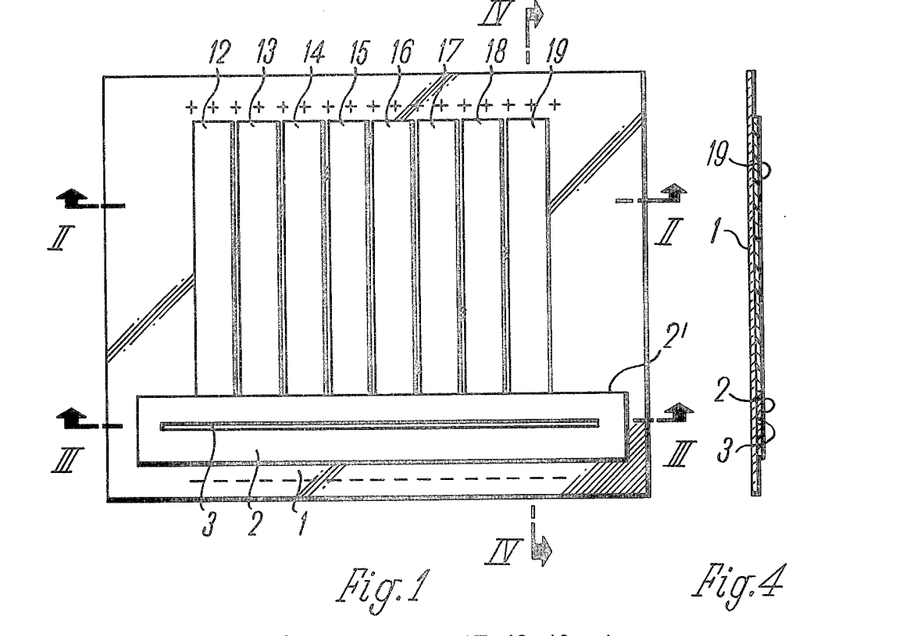
FIG. 1 is a schematic representation of a first exemplary embodiment of an apparatus which may be used in carrying out the method of the invention in a top view and before use.
FIG. 4 is a section along the line IV—IV in FIG.
Figure 2:
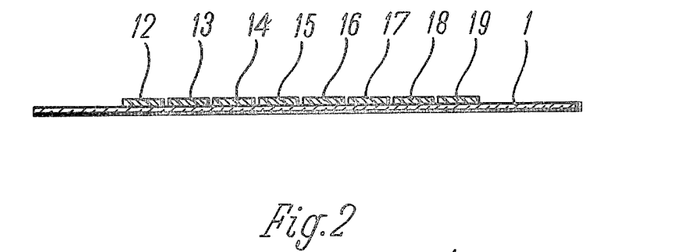
FIG. 2 is a section along the line II—II of FIG. 1.
Figure 3:
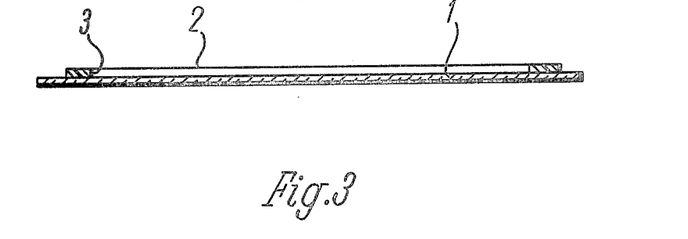
FIG. 3 is a section along the line III—III in FIG. 1.

Vertically adjacent to the strip 2 are several further strips 12, 13, ... 19. Each of these secondary strips also consists of agarose gel but each of the vertical strips includes a different and precisely determined amount of a specific antibody. Each of the antibodies of each individual strip 12, 13 ... 19 is directed to act against a specific one of those antigens which might be included in the sample contained in the well 3 and which are to be determined during the examination. If the sample is blood plasma, each of the strips 12, 13, ... 19 wuld contain antibodies directed against one and only one plasma protein.

It follows that, within each of the strips 12, 13, ... 19, only one of the plasma proteins contained in the sample can produce a precipitate by immunoreaction with the particular antibody to which it is specific. In the examination of blood plasma, this means that, in each of the strips, a different plasma protein from the sample in the well 3 forms a precipitate by immunoreaction with the monospecific antibody contained in that strip.

Figure 5:
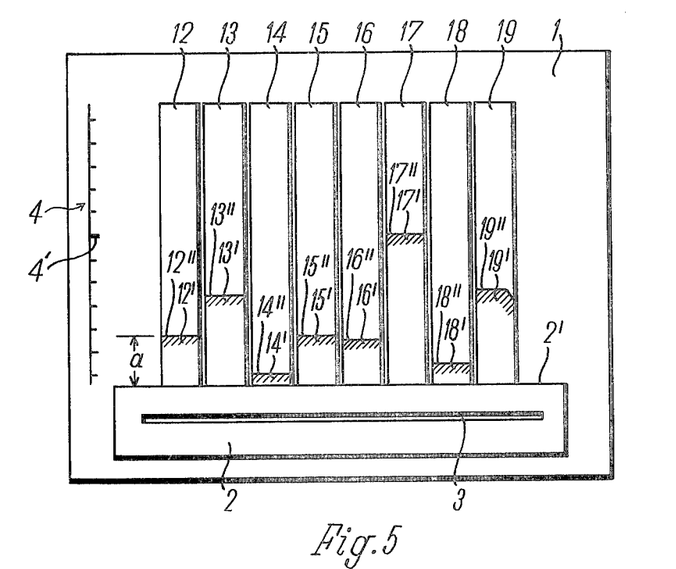
FIG. 5 is a schematic representation of the apparatus of FIG. 1 after a test on the sample has been performed.

If the well 3 is filled with a sample, for example blood plasma, containing several antigens (or generally several substances effective as antigens) and if an electric field is now applied as indicated in FIG. 1 by the minus signs at the bottom of the strip 2 and the plus signs at the top ends of the strips 12, 13, . . . 19, then the individual constituents of the sample, i.e., the individual antigens, migrate within the antibody-free agarose gel of the strip 2 in the upward direction as seen in the figure, past the upper edge 2' into the adjacent strips 12, 13, . . . 19. Since, as already mentioned, these individual strips contain monospecific antibodies directed against different ones of the antigens within the sample, only a single immunoreaction takes place in each strip. The precipitated complexes are then redissolved by the excess antigens. Only when there is no longer an excess of antigens, i.e., when the entire supply of some antigen contained in the sample is used up by immunoreaction against the antibodies contained within one of the strips, do the precipitates remain stationary, and thus their limits become recognizable, possibly after staining. Thus there is produced a picture as shown schematically in FIG. 5. In FIG. 5, the various precipitates are designated by numerals 12', 13', . . . 19' and are indicated by hatched lines. The limits of the precipitate are designated with the numerals 12", 13" . . . 19" and are clearly recognizable.

The position of the limits of precipitation 12", 13" . . . 19", in the direction in which the antigens migrated from the well 3 into the various strips and which is also the direction of the applied electric field, is a measure of the concentration of the particular antigens in the blood plasma sample. In particular, the position of the precipitate limit 12" is a measure of the concentration of that antigen in the blood plasma sample which formed an immunoreaction with the antibodies contained in the strip 12. Similarly, the position of the precipitate limit 13" is a measure of the concentration of the antigen reacting with the antibody in strip 13, etc.

The plate 1 shown in FIG. 5 is provided with a scale of indicia 4 which permits an easy quantification of the position of the precipitate limits, i.e., their distance a from the upper edge 2' of the strip 2 or from the lower edge of the strips 12, 13, . . . 19, respectively.

When human blood plasma is examined, it is possible to so adjust the concentration of the individual antibodies within the strips 12, 13, . . . 19 that when, for example, the blood plasma of a healthy human patient is examined, all the precipitate limits would lie at the same height, for example along the marker 4'. Thus, when the blood plasma of a diseased patient is examined under the same conditions, the deviations of the concentration of particular plasma proteins from the normal value would thus be recognizable in an extremely simple manner since the precipitate limits of those strips which contain antibodies against the particular plasma proteins would be above or below the marker 4'. Typical patterns of deviation from the normal values could thus be associated with particular pathological syndromes, which represents a considerable progress and substantially facilitates the medicinal diagnosis. The above-recited statement, namely that the distance a of the precipitate limits 12", 13", . . . 19" from the upper edge 2' of the strip 2 or from the lower ends of the strips 12, 13, . . . 19 depends on the concentration of the antigens which immunoreact with the antibodies in the strips, has been demonstrated in experiments of which two are now described.

EXPERIMENT NO. 1

This experiment is made to show that the distance "a" of the precipitate limits from the upper edge 2' of the strip 2 depends on the concentration of the monospecific antibodies contained in the strips 12, 13, . . . 19 against one particular, specific antigen-effective component of the sample. It is further to be shown that, the larger a becomes, the fewer antibodies are present in the strips 12, 13, . . . 19 and vice versa.

Figure 6:
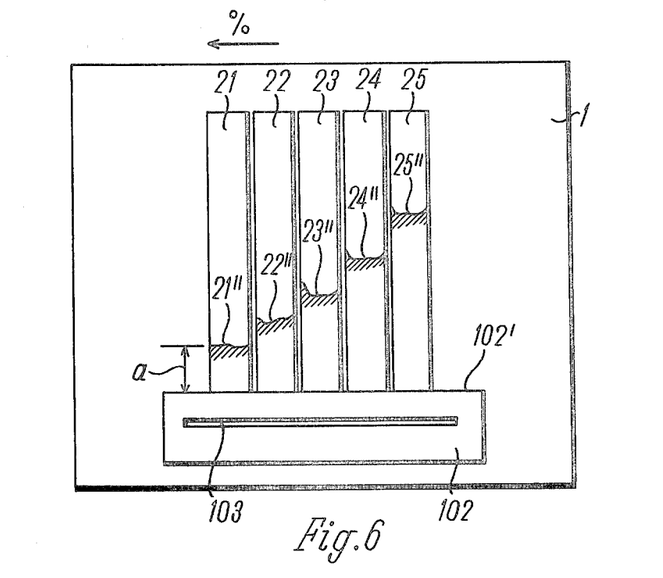
FIG. 6 is a representation of an experiment further explaining the invention (Experiment No. 1)

The results of the experiment 1 are shown in FIG. 6. The strips 21, 22, . . . 25 of a width of approximately 10 millimeters and a length of approximately 72 millimeters each contained antibodies against a particular plasma protein, namely against $a_2$ Macroglobulin, but in different concentrations. The strips 21, 22, 23, 24, 25 contained, respectively, 160, 120, 80, 60 and 40 microliters antiserum against $a_2$ Macroglobulin. The well 103 in the strip 102 was filled with approximately 200 microliters of a mixture of 300 microliters blood plasma of a healthy blood donor and 0.7 milliliters agarose. It is necessary to mix the plasma sample with agarose prior to application in the well 103 so as to guarantee a uniform continuous electrical conductivity in the agarose gel after filling the well 103 with the electrically conductive agarose even after the sample has migrated into the strips 21 to 25 or into the strips 12, 13, . . . 19 of FIG. 5.

The experiment resulted in the following distances a of the precipitate limits 21", 22". . . 25" from the upper edge 102' of the strip 102:

| Strip No. | Table of results of Experiment No. 1 | |
|---|---|---|
| | Microliters Antiserum in Strip | Distance of the Precipitate (Mean Value) (mm) |
| 21 | 160 | 7 |
| 22 | 120 | 9,5 |
| 23 | 80 | 13 |
| 24 | 60 | 17,5 |
| 25 | 40 | 24 |

This experiment clearly shows that the distance a of the precipitate limits 21". . . 25" is a function of the antibody content in the strips 21 . . . 25, i.e., the lower the antibody content in this strip, the greater is the distance a of the precipitate limit from the lower ends of the strips 21, 22 . . . 25 which are adjacent to the upper edge 102' of the strip 102. Conversely, it is also shown that, the larger the antibody content in the strips, the smaller is the distance a.

EXPERIMENT NO. 2

Figure 7:
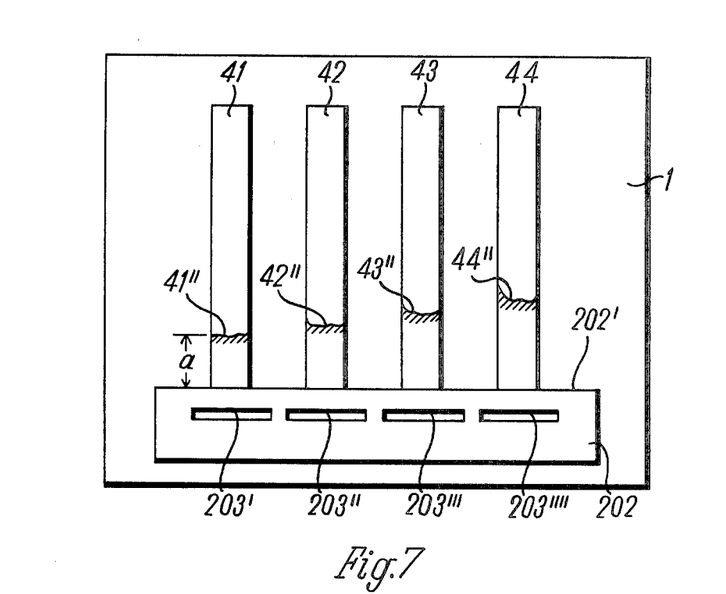
FIG. 7 is a schematic representation of the results of a second experiment for explaining the invention (Experiment No. 2)

It is the purpose of experiment No. 2 to demonstrate that the distance "a" of the precipitate limits from the lower ends of the strips or the upper edge 2' of strip 2 in FIG. 5 depends on the quantity of the applied sample or, if the sample volume is constant, on the concentration of that component within the sample which immunoreacts with the antibodies in the strips. The results of this experiment are shown in FIG. 7. The strips 41 to 44 contain antibodies against $a_2$ Macroglobulin in equal concentration, i.e., each of these strips contained 60 microliters anitserum against $a_2$ Macroglobulin. In order to obtain in each strip an immunoraction with $a_2$ Macroglobulin of different concentrations, four separate wells 203', 203", 203'" and 203"" were made in the strip 203. The serum of a healthy blood donor was placed in these wells in different concentrations in a solution of agarose. The different concentrations of equal volume of sample in the wells are given in the following table. Otherwise, the experimental conditions were the same as those in Experiment 1. The table also shows the different distances "a" of the precipitate limits from the upper edge 202' of the strip 202.

| | | Table of Results for Experiment 2 | |
|---|---|---|---|
| Strip No. | Well No. | Microliters of Serum per 100 Microliters of Sample | Distance a of the Precipitate Limit (Mean Value) (mm) |
| 41 | 203' | 26 | 11 |
| 42 | 203'' | 36 | 14 |
| 43 | 203''' | 46 | 17 |
| 44 | 203'''' | 56 | 20 |

This experiment shows that, for a constant antibody concentration in the strips 41, 42, 43, 44, the distance "a" of the precipitate limits is a function of the applied sample quantity or, if the sample quantity is constant, it is a function of the concentration of the components in the sample which undergo immunoreaction.

The results of the two experiments, when taken together, show that the distance "a" is a function of two parameters, firstly of the antibody concentration in the strips 12, 13, . . . 19 and also of the antigen concentration in the sample. This also implies that, when the antibody concentration in the strips 12, 13, . . . 19 is known, then the distance "a" is a measure of the concentration of the antigen-effective substance in the probe with which the antibodies have produce an immunoreaction.

In order to cause or enhance the migration of the sample placed in the well 3 into the antibody-containing strips 12, 13, . . . 19, an electric field is applied to the strips for a duration of at least eight hours (for example overnight). With a suitable electric field strength, after this period of time, all antigens have usually completely reacted with their corresponding antibodies. Inasmuch as the precipitates in the agarose gel are immovable after a completed reaction, a more prolonged application of voltage (for example 24 hours) would not alter the position of the precipitate limits.

The application of the electric potential may be performed with any customary and known electrophoretic apparatus, i.e., in principle by two electrodes which are applied via buffer solutions at the locations indicated in FIG. 1 with plus and minus signs, respectively. The electric field strength is approximately 8 volts per centimeter.

The process which takes place in the individual strips is the formation of a precipitate by immunoreaction under the influence of an electric field, thus the process may be called an electro-immuno-precipitation. The buffer solution (a barbiturate buffer of pH 8.6 at 0.2 M) is used to insure a constant buffered pH of 8.6 within the agarose gel. At this pH value, the antibody molecules in the strips have neither positive nor negative excess charge and thus do not migrate under the influence of the applied electric field as do the individual components of the applied solution. They form instead a stationary phase into which the mobile antigen molecules of the sample migrate.

However, at the preferred pH of 8.6, the blood plasma contains individual proteins which do not have the negative charge common to most of the proteins which migrate into the strips under the influence of the applied field, but are electrically neutral or may even be positively charged. Proteins falling into this group are the immunoglobulins Ig G, Ig M, Ig A, Ig D as well as the C-reactive protein and Fibrinogen. The charge of these plasma proteins (as well as that of all other antigen-effective substances without or with reverse charge) can also be changed chemically for a given pH of 8.6 so as to migrate into the strips under the influence of the electric field. This may be done by a prior treatment of the sample with formaldehyde. Instead of formaldehyde, the prior treatment may be performed with β-propiolacton or with potassium cyanate (KCNO).

It is also suitable to add to the sample placed in the well 3 a well defined quantity of a further, foreign antigen-effective substance. For example, one may add to a blood plasma sample a particular quantity of ovalbumin, not contained in the blood plasma, to serve as an internal standard and further to add to all strips 12, 13, . . . 19 a well-defined quantity of antibodies against this substance, i.e., for example antibodies against ovalbumin. In that case, there is formed in each of the strips 12, 13, . . . 19 a second precipitate whose limit can be used as a reference, i.e., as a standard magnitude, because it is formed under the same overall conditions as are the precipitate limits of the substances within the sample, and, in addition, the quantity of the antibodies in the strips, as well as the concentration in the sample, will be known in advance. If the internal standard is in hand and the concentration in the applied sample is also known, then the quantity of sample no longer affects the quantitative analysis and thus is eliminated as a source of error. In that case, the place of the distance "a" as described for the exemplary embodiment of FIG. 5 is taken by a distance "b" between the two precipitate limits within a strip and this distance "b" then provides a measure for the concentration of the antigen-effective substance within a sample, against which the antibodies in that particular strip are effective.

Figure 8:
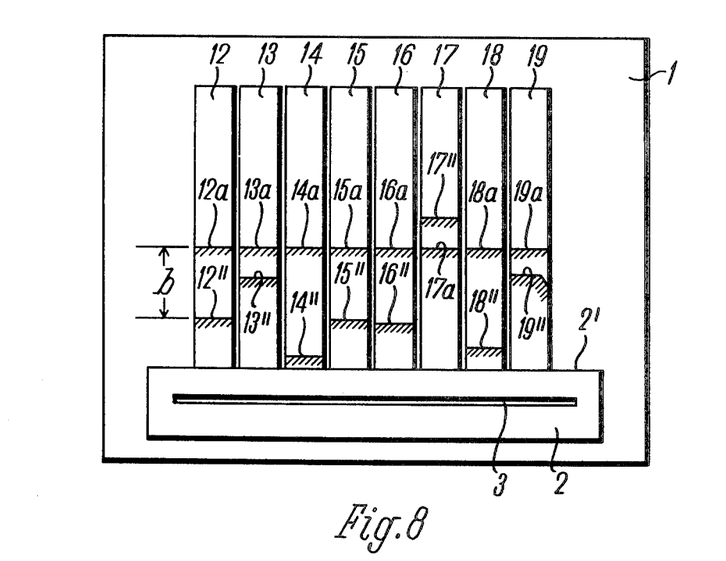
FIG. 8 is a top view of a second exemplary embodiment of the apparatus according to the invention after use.

An exemplary embodiment of this type is illustrated in FIG. 8. Shown there are, in each case, second precipitate limits 12a, 13a, . . . 19a which refer to the internal standard and which are always at the same height, i.e., they are at the same distance from the upper edge 2' of the strip 2. In this case, it is the distances "b" between the precipitate limits 12'' and 12a, etc., which are a measure for the concentration of the antigen effect of substances in the sample against which the antibodies contained in the strips 12, 13, . . . 19 are specifically directed.

The results of two individual determinations of blood plasma proteins in a sample of blood plasma taken with the apparatus of the two above-described exemplary embodiments will now be described:

FIRST EXEMPLARY EMBODIMENT

The experiment used a plate 1 on which, as shown in FIG. 1, eight strips were located. 0.25 ml of serum from a healthy blood donor was mixed with 1 ml of a mixture containing 0.4 M formaldehyde in a 0.015 M barbital buffer and this final mixture was left standing at room temperature for 30 minutes. Subsequently, this mixture was further mixed with 1.250 ml agarose. 0.75 ml of this mixture was placed in the well 3. The strips 12, 13, . . . 19 contained monospecific antisera against particular antigens contained within the blood plasma sample whose quantity was to be determined (compare the table relating to the first exemplary embodiment). The width of each strip was approximately 10 mm and its length approximately 74 mm. The quantity of antisera in the strips is given in the following table as are the distances "a" of the precipitate lines from the upper edge 2' of the strip 2 as obtained in the experiment.

TABLE FOR THE FIRST EXEMPLARY EMBODIMENT

Table for the First Exemplary Embodiments

| Strip No. | Quantity and Type of Antiserum contained in the strip (μl) | Distance "a" (Mean value) (mm) |
|---|---|---|
| 1 | 100 Anti-IgG | 23 |
| 2 | 100 Anti-IgM | 2 |
| 3 | 100 Anti-IgA | 16,5 |
| 4 | 50 Anti-Lipoprotein | 11 |
| 5 | 50 Anti-$\alpha_2$-Macroglobulin | 11 |
| 6 | 100 Anti-Haptoglobin | 21,5 |
| 7 | 50 Anti-Ceruloplasmin | 4,5 |
| 8 | 150 Anti-Acidic α-1-Glycoprotein | 9 |

Figure 9:
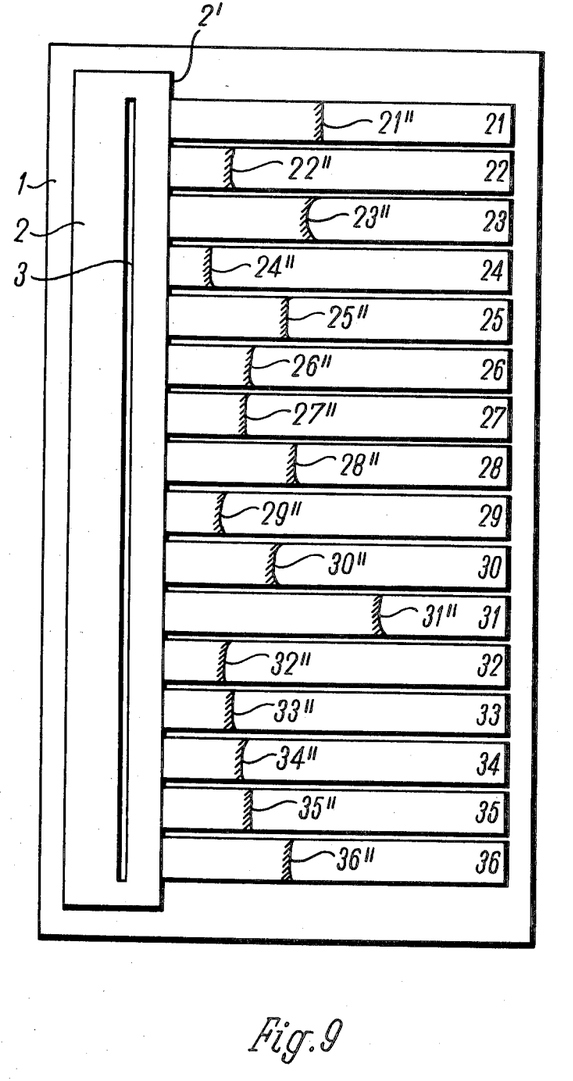
FIG. 9 is a top view of a further exemplary embodiment of the invention.

SECOND EXEMPLARY EMBODIMENT 0.250 ml of fresh blood plasma from a healthy donor was well mixed with 1.0 ml of a solution of formaldehyde (0.4 M formaldehyde in 0.015 M barbital buffer) and incubated at room temperature for thirty minutes. Subsequently, 4 ml of agarose was added and a total of 5 ml of this final mixture was placed into the well 3 of a plate, as shown in FIG. 9, containing 16 strips 21, 22, . . . 36. The strips 21, 22, . . . 36 contained quantities of a monospecific type of antibody against the shown plasma proteins as shown in the following table relating to the second exemplary embodiment. An electric potential was applied, resulting in an electric field of 8 volts per cm and, subsequently, the distance "a" of the precipitate limits 21", 22", . . . 36" was measured. The following distances (mean values) were obtained.

| Strip No. | Quantity and type of Antiserum contained in the strip (μl) | Distance a (Mean value) (mm) |
|---|---|---|
| 21 | 50 Anti-Fibrinogen | 33 |
| 22 | 50 Anti-Plasminogen | 13 |
| 23 | 75 Anti-Orosomucoid | 30 |
| 24 | 100 Anti-Antichymotrypsin | 9 |
| 25 | 150 Anti-α-I-Antitrypsin | 26 |
| 26 | 50 Anti-Ceruloplasmin | 18 |
| 27 | 50 Anti-α-2-Macroglobulin | 17 |
| 28 | 100 Anti-Haptoglobin | 28 |
| 29 | 75 Anti-Hemopexin | 12 |
| 30 | 100 Anti-Transferrin | 24 |
| 31 | 100 Anti-α-Lipoprotein | 47 |
| 32 | 100 Anti-β-Lipoprotein | 13 |
| 33 | 50 Anti-$\beta_1$-C/$\beta_1$ A Globulin | 15 |
| 34 | 100 Anti-IgA | 17 |
| 35 | 30 Anti-IgM | 19 |
| 36 | 100 Anti-IgG | 28 |

Figure 10:
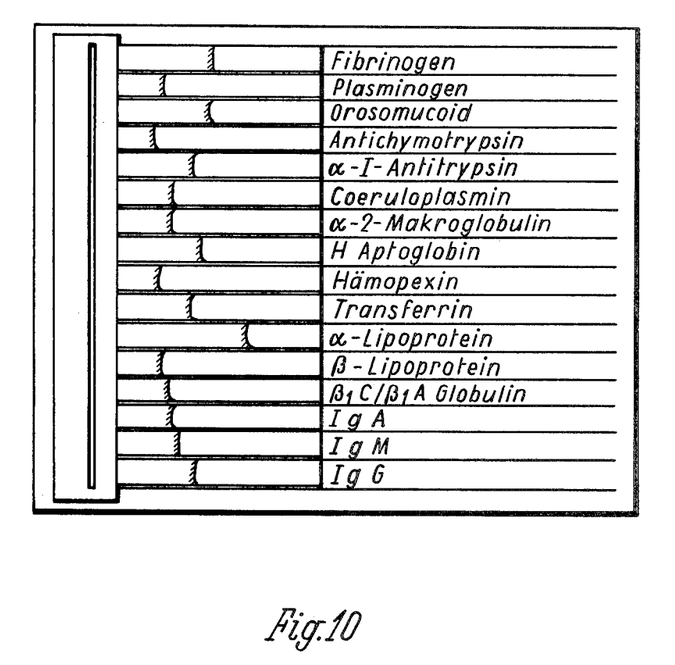
FIG. 10 is a representation of a photograph of the exemplary embodiment according to FIG. 9 in which the individual carriers have been identified.

FIG. 10 is a schematic representation of this type of plate after a test was made; it was photographed and labeled according to the type of antiserum used. After staining, the precipitate limits are clearly recognizable in the individual strips. It is seen that, for each of the examined 16 plasma proteins in the second exemplary embodiment, a clearly visible and hence measurable precipitate was formed in the appropriate strip. The plasma proteins which were chosen and shown to be quantifiable simultaneously from the same sample represent those plasma proteins which have been recognized at the present time to be most useful for diagnostic purposes: fibrinogen and plasminogen are decisive for the diagnosis of blood coagulation disturbances; orosomucoid, antichymotrypsin, antitrypsin and ceruloplasmin are typically increased in concentration in cases of acute and chronic inflammations as well as in the case of carcinoma; $\alpha_2$-macroglobulin is important in the diagnosis of certain kidney diseases; the simultaneous determination of haptoglobin, hemopexin and transferrin permits a differential diagnosis of anemic diseases; α- and especially β-Lipoprotein is important in the recognition of disturbances in fat metabolism which, in turn, represent a risk factor for the generation of arteriosclerosis; $\beta_1$C/$\beta_1$ A-globulin indicates disturbances in the complementary system; Ig A, Ig M and Ig G are increased or decreased in a typical manner for specific diseases, especially for infections, allergic diseases, liver diseases, inflammations and malignant tissue growths. In summary, the results indicate the wide range of useful possibilities in differential diagnosis which is made possible by the invention.

The plates used in the exemplary embodiments, which are provided with the strips acting as carriers for the antisera, may be produced as follows: As already described above, antibody-free agarose gel is applied as a strip to a glass plate. Subsequently, the desired number of strips 12, 13, . . . 19 is applied, the exact number corresponding to the number of antigen-effective substances to be determined. This is also done by applying warm agarose gel at approximately 50° C containing the predetermined number of antibodies, by pouring in strips and subsequent cooling at room temperature, where the gel solidifies. The dosaging of antibodies in the agarose gel, of which the individual strips 12, 13, . . . 19 are made, takes place on the basis of appropriate tests; for example, when blood plasma is examined, the normal values of the concentration of each blood plasma protein should result in an approximately equally high extent of the precipitate (distance a of the precipitate limit from the lower end of the strip) so that deviations from the normal values may be easily noticed by deviations from this straight, normal line which passes through all strips.

The special advantage of this simultaneous quantitative determination of several antigen-effective substances in a sample, for example of plasma proteins in blood plasma, is that particular strips in a plate may be infused with antibodies against exactly those plasma proteins which are subject to deviations for a particular pathological syndrome (cardiac infarct, pneumonia, inflammation, tumors, etc.), thus creating an important tool for differential diagnosis.

Figure 11:
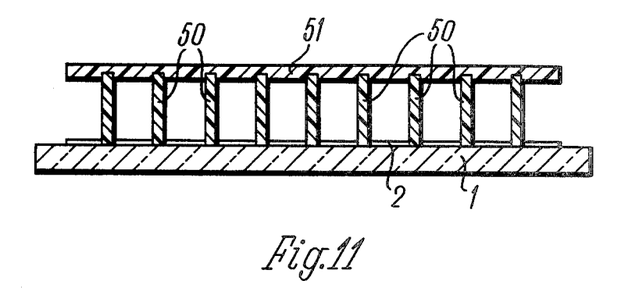
FIG. 11 is a device useful for manufacturing the apparatus according to the invention.
Figure 12:
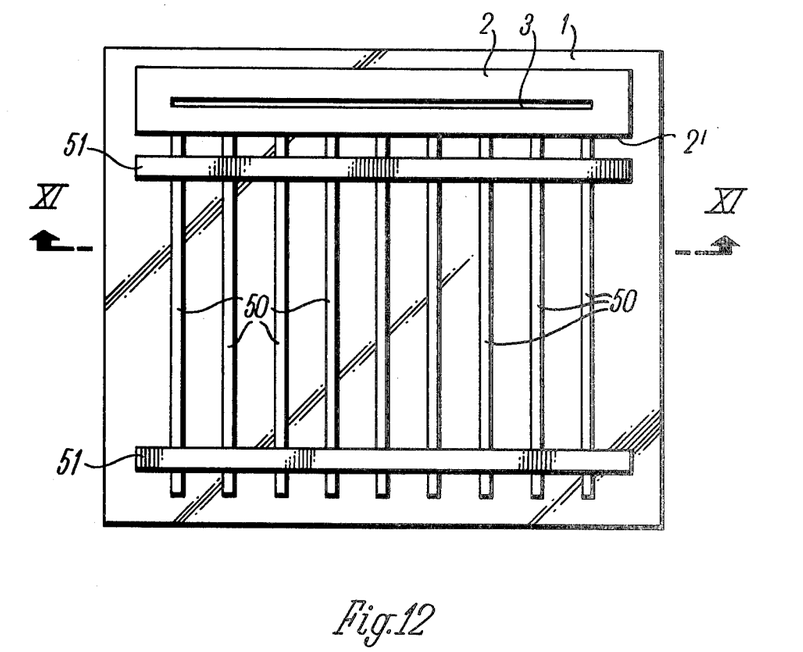
FIG. 12 is a top view of the device according to FIG. 10.

In FIGS. 11 and 12, there is shown a relatively simple device for producing these strips 12, 13 . . . 19 on a plate 11. This device consists of vertically extending plates 50 held together by two rails 51. This device is placed so that the ends of the plates 50 are adjacent to the edge 2' of the strip 2. Subsequently, the intermediate spaces between the plates 50 are then filled with agarose containing different monospecific antibodies, thereby forming the strips 12, 13, . . . 19. The application of the electric field does not require special means because, as already explained, all known electrophoretic instruments or simple devices assembled from elementary electrodes may also be used.

The parallel orientation of the strips as shown in the preferred embodiments is not a necessary requirement, nor do the strips have to be necessarily rectangular. Radial patterns of several strips can also be used. The strips may, in that case, have the shape of circular segments providing that the resulting greater non-linearity of the distance "a" of the precipitate limits from the beginning of the strip can be tolerated in certain special cases of investigation.

As already mentioned, a further variation of the invention is possible by including in the strips 12, 13, . . .

19 of FIG. 5, not antibodies as previously described, but rather antigens, and thus to investigate the individual components of samples containing antibodies. A field of application of this variant method would be the diagnosis of autoimmuno diseases and allergies. In that case, tissue extracts of the different tissues, such as heart, kidney, muscle, thyroid gland and nucleic acids would be incorporated in the strips. The sample to be placed in the well 3 would be patient serum. If the patient serum contains autoantibodies against a particular type of tissue, then precipitates will be formed in the strip containing that particular tissue extract, whereas all other strips which contain tissue extracts against which the patient serum does not contain autoantibodies would be traversed by the sample without forming a precipitate.

What is claimed is:

1. A method for the simultaneous qualitative and quantitative analysis of a plurality of immunoreactive substances, especially of antigen-effective substances contained in a sample, comprising the steps of:
   A. placing the sample to be tested in a first carrier material which is free from antibodies;
   B. providing a second carrier material, adjacent to said first carrier material, said second carrier material containing ingredients capable of undergoing immunoreactions with said substances in said sample, thereby forming precipitates;
   C. causing the migration of said sample from said first carrier material into said second carrier material;
   D. applying an electric field to the area of said first and second carriers for enhancing the migration of said sample from said first carrier material into said second carrier material substantially in the direction of said electric field; the improvement comprising the steps of:
   E. providing a plurality of second carrier materials, simultaneously adjacent to said first carrier material, and
   F. providing in each of said plurality of second carrier materials a different ingredient, each different ingredient being capable of undergoing a precipitate-forming immunoreaction with one of the substances to be analyzed in said sample.

2. A method as defined in claim 1, further comprising the step of:
   G. treating the sample to alter the chemical electric charge on the molecules in said sample so as to obtain a negative effective charge.

3. A method as defined in claim 2, wherein the sample is treated with a chemical from the group comprising $\alpha$ and $\beta$-propiolactene and potassium cyanate.

4. A method as defined in claim 2, wherein the sample is treated for approximately 30 minutes at approximately 20° Centigrade.

5. A method as defined in claim 1, wherein the step of applying an electric field includes applying an electric field of approximately 8 volts centimeter for approximately 8–10 hours.

6. A method as defined in claim 1, further comprising the steps of:
   H. adding to the sample a known concentration of a known calibrating substance different from any substance to be analyzed;
   I. adding to each of said second carrier materials a calibrating ingredient different from said ingredients which undergo immunoreaction with said substances to be analyzed, said calibrating ingredient being capable of undergoing an immunoreaction with said calibrating substance.

7. A method as defined in claim 1, wherein the concentration of ingredients in said plurality of second carrier materials is so chosen that, when a sample with a predetermined concentration of antigen-effective substances is placed in said first carrier material, the immunoprecipitates formed in each of said plurality of second carrier materials all have substantially the same geometrical extent, as measured from the limits of said first carrier material.

8. A method as defined in claim 1, wherein said antigen-effective substances are antigens.

9. A method as defined in claim 1, wherein said sample is blood plasma and said antigen-effective substances are plasma proteins.

10. A method as defined in claim 1, wherein said sample is blood serum and said ingredients in said second carrier materials are different tissue extracts; whereby the resulting precipitates are indicators of the phenomenon of auto-immunoreaction.

* * * * *